(12) United States Patent
Fujieda et al.

(10) Patent No.: US 10,213,543 B2
(45) Date of Patent: Feb. 26, 2019

(54) BLOOD PURIFICATION COLUMN

(71) Applicant: Toray Industries, Inc., Tokyo (JP)

(72) Inventors: Hiroaki Fujieda, Otsu (JP); Yoshiyuki Ueno, Otsu (JP); Kazumi Tanaka, Otsu (JP)

(73) Assignee: Toray Industries, Inc. (JP)

( * ) Notice: Subject to any disclaimer, the term of this patent is extended or adjusted under 35 U.S.C. 154(b) by 460 days.

(21) Appl. No.: 14/765,386

(22) PCT Filed: Feb. 7, 2014

(86) PCT No.: PCT/JP2014/052889
§ 371 (c)(1),
(2) Date: Aug. 3, 2015

(87) PCT Pub. No.: WO2014/126014
PCT Pub. Date: Aug. 21, 2014

(65) Prior Publication Data
US 2015/0374898 A1 Dec. 31, 2015

(30) Foreign Application Priority Data
Feb. 12, 2013 (JP) ................................. 2013-024040

(51) Int. Cl.
*A61M 1/14* (2006.01)
*A61M 1/36* (2006.01)
(Continued)

(52) U.S. Cl.
CPC ............ *A61M 1/3679* (2013.01); *A61M 1/14* (2013.01); *A61M 1/36* (2013.01); *A61M 1/3627* (2013.01);
(Continued)

(58) Field of Classification Search
CPC .............. A61M 1/3679; A61M 1/3627; A61M 1/3643; A61M 1/3672; A61M 2205/75;
(Continued)

(56) References Cited

U.S. PATENT DOCUMENTS 5,139,668 A * 8/1992 Pan .................... B01D 15/00
210/321.8
5,961,931 A * 10/1999 Ban .................... B01D 39/2041
422/171
(Continued)

FOREIGN PATENT DOCUMENTS

| JP | 59-95051 A | 5/1984 |
|---|---|---|
| JP | 6-53168 B2 | 7/1994 |

(Continued)

*Primary Examiner* — Katherine Zalasky
*Assistant Examiner* — Benjamin L Lebron
(74) *Attorney, Agent, or Firm* — DLA Piper LLP (US)

(57) ABSTRACT

A blood purification column includes an adsorbent and a casing whose two ends are open ends, wherein the adsorbent is housed inside the casing, and wherein one of two casing ends is a blood inflow-side end portion and another is a blood outflow-side end portion, and wherein a filter is disposed at the blood inflow-side end portion and/or the blood outflow-side end portion of the casing, and wherein the filter satisfies (1)-(3):
(1) an opening rate thereof is greater than or equal to 5% and less than or equal to 80%;
(2) an equivalent diameter of an aperture thereof is greater than or equal to 1 μm and less than or equal to 5000 μm;
(3) a ratio of the equivalent diameter of the aperture thereof to an average circle equivalent diameter of void spaces of the adsorbent is greater than or equal to 45%.

8 Claims, 5 Drawing Sheets

(51) Int. Cl.
*B01J 20/26* (2006.01)
*B01J 20/28* (2006.01)
*A61M 1/10* (2006.01)

(52) U.S. Cl.
CPC ........ *A61M 1/3643* (2013.01); *A61M 1/3672* (2013.01); *B01J 20/26* (2013.01); *B01J 20/261* (2013.01); *B01J 20/262* (2013.01); *B01J 20/28* (2013.01); *B01J 20/2805* (2013.01); *B01J 20/28023* (2013.01); *A61M 1/1006* (2014.02); *A61M 2205/75* (2013.01); *B01J 20/28019* (2013.01)

(58) Field of Classification Search
CPC ........ A61M 1/1006; A61M 1/14; A61M 1/36; B01J 20/261; B01J 20/262; B01J 20/28023; B01J 20/2805; B01J 20/26; B01J 20/28; B01J 20/28019
See application file for complete search history.

(56) References Cited

U.S. PATENT DOCUMENTS

| | | | |
|---|---|---|---|
| 5,980,612 A * | 11/1999 | Kelly | B01J 20/3441 95/106 |
| 6,241,886 B1 * | 6/2001 | Kitagawa | B01D 39/083 210/483 |
| 6,416,293 B1 * | 7/2002 | Bouchard | A61M 1/1037 137/599.14 |
| 2004/0222144 A1 | 11/2004 | Nakatani et al. | |
| 2005/0001076 A1 * | 1/2005 | Eicher | A61M 11/06 239/590 |
| 2007/0227967 A1 * | 10/2007 | Sakaino | B01L 3/502753 210/502.1 |
| 2010/0176048 A1 * | 7/2010 | Sakaguchi | A61L 31/16 210/321.62 |
| 2011/0033704 A1 * | 2/2011 | Nakao | A61M 1/3679 428/398 |
| 2013/0306544 A1 * | 11/2013 | Ueno | B01D 63/02 210/321.79 |

FOREIGN PATENT DOCUMENTS

| | | | | |
|---|---|---|---|---|
| JP | 2003-225304 A | | 8/2003 | |
| JP | 2009-254695 A | | 11/2009 | |
| JP | 2010-148851 A | | 7/2010 | |
| JP | WO 2012091028 A1 * | | 7/2012 | ............ B01D 63/02 |
| WO | 2002/060512 A1 | | 8/2002 | |
| WO | 2013/129384 A1 | | 9/2013 | |

* cited by examiner

BLOOD PURIFICATION COLUMN

TECHNICAL FIELD

This disclosure relates to a column used for blood purification and the like, and relates to a blood purification column excellent in air removal characteristic and is unlikely to induce in-circuit blood coagulation at the time of blood introduction, and the like.

BACKGROUND

A therapeutic method called apheresis therapy in which blood of a patient is temporarily taken out of the body, etiologic substances in the taken-out blood are removed by a process such as adsorption or filtration, and the blood is then returned into the patient's body is known. That apheresis therapy is utilized in therapy for drug intoxication, food intoxication, and familial hypercholesterolemia, therapy for autoimmune diseases such as ulcerative colitis, Crohn's disease, articular rheumatism and the like, and is used to remove from the blood of a patient substances such as drugs, toxins and cholesterol, and inflammatory cells such as white blood corpuscles and blood platelets, which are considered to be causes of the diseases indicated above.

As apheresis therapies as indicated above, a double membrane filtration plasma exchange therapy (DFPP: Double Filtration Plasmapheresis) in which plasma is separated from blood by using a primary membrane and then the plasma is passed through a secondary membrane, and a direct blood perfusion therapy (DHP: Direct Hemo Perfusion) in which a body fluid of a patient is directly processed are known. The DHP, whose process is simple and convenient, is rapidly spreading in recent years. As for the form in which the column for use in the DHP is used, there exists, besides the form in which the column is used singly, a form in which in dialysis performed on a patient with renal failure or the like, the column is used by linking it in series to an artificial kidney, whereby β2-microglobulin, which is a causative substance for dialysis-related amyloidosis, which is a dialysis complication, and the like can be efficiently adsorbed.

In the DHP as described above, blood is passed through a column within which an adsorbent is housed, and removal-object substances in the blood are adsorbed to and removed by the adsorbent. A column as indicated above usually has a hollow cylindrical casing at whose two ends in a lengthwise direction there are disposed header caps provided with an inflow opening or an outflow opening for blood. An adsorbent is housed inside this casing. By disposing filters having many small openings at an end portion of the casing via which blood flows in and an end portion via which blood flows out, it becomes possible to hold the adsorbent within the casing.

Generally, when a blood purification column is used as a medical instrument in the DHP or the like, a so-called priming operation in which the column, before being used, is subjected to the passage of and the filling with physiological saline or the like. At this time, if air occurs in the column or the circuit and resides in the column, the air impedes the passage of and the filling with physiological saline or the like and the contact areas between the adsorbent and blood is reduced so that a decline in the adsorption-removal performance of the blood purification column is sometimes brought about. Furthermore, in a column in which a filter disposed at an end portion of the column is poor in air removal, that is, column that has a filter through which when air is once taken into the column the air is not easily removed to the outside of the column, blood in the column is likely to be activated to coagulate due to air that remains in the column. In particular, in a column used in a form in which the column connects in series to an artificial kidney as stated above, the washing (priming) of the column and the artificial kidney performed prior to the therapy is preferred to be performed in a state where the column and the artificial kidney connect in series from the viewpoint of operability. However, when as the artificial kidney, an artificial kidney in a moist state or a dry state and not filled with water is used, a large amount of air flows into the column. Therefore, as for the filter for use in the column, a property excellent in air removal and, at the same time, excellent in biocompatibility, that is, that is unlikely to induce in-circuit coagulation or the like at the time of blood circulation, is required. Up to the present, patents that indicate that a mesh is used for fixation of an end portion of a column for use in the DHP have existed (Japanese Unexamined Patent Publication (Kokai) No. 59-95051 and Japanese Unexamined Patent Publication (Kokai) No. 2009-254695). However, as for a mesh, there is only a description that a mesh designed to be capable of retaining an adsorbent within a column should be used, and there is no description about bettering the aforementioned air removal characteristic by a design of a mesh. Furthermore, there is also an invention in which meshes are provided at two ends of a column that, as an adsorbent within the column, uses an adsorbent made up of fiber in a hollow yarn state or a solid yarn state (Japanese Unexamined Patent Publication (Kokai) No. 2010-148851). However, that invention, too, does not discuss air removal. On the contrary, the meshes are created by rolling the adsorbent with a web-state cloth for the purpose of stably retaining the in-column adsorbent or improving the in-column flow. Disposing such a mesh that is open parallel with the column longer-axis direction is not preferable from the viewpoint of air removal characteristic.

It could therefore be helpful to provide a filter contained in a blood purification column and improve the removal characteristic regarding air that gets into the column and to prevent blood activation due to air remaining in the column and decreased adsorption performance due to a decrease in the contact area between blood and an adsorbent.

SUMMARY

We thus provide a blood purification column having an adsorbent and a casing whose two ends are open ends, wherein an adsorbent is housed inside the casing, and wherein one of the two casing ends is a blood inflow-side end portion and another is a blood outflow-side end portion, and wherein a filter is disposed at the blood inflow-side end portion and/or the blood outflow-side end portion, and wherein the filter satisfies conditions as follows:

(1) an opening rate is greater than or equal to 5% and less than or equal to 80%;
(2) an equivalent diameter of an aperture is greater than or equal to 1 μm and less than or equal to 5000 μm;
(3) a ratio of the equivalent diameter of the aperture to an average circle equivalent diameter of void spaces of the adsorbent is greater than or equal to 45%.

With regard to the foregoing (3), the housed adsorbent has therein void spaces, and we found that the aforementioned equivalent diameter of the filter aperture and the aforementioned average circle equivalent diameter of void spaces of the adsorbent are closely related and that by making proper the ratio between the two, the air removal characteristic is improved.

Further, as for the filter, the hydrophilicity and -phobicity is important, and namely, a filter whose material's contact angle is in a proper range is preferable. Therefore, as for the material of the filter, at least one kind of material selected from polyolefin-based resin, polyamide-based resin, and fluorine-based resin is preferred to be contained, and at least one material selected from polypropylene, polyethylene, nylon 6, nylon 66, and their derivatives is more preferred to be contained, and, still more preferably, at least any one of polypropylene and its derivatives is contained.

We can thus provide a blood purification column capable of efficiently removing air that occurs at the time of priming operation, which is performed before use, to the outside of the column and is less likely to allow occurrence of in-circuit coagulation at the time of blood circulation.

EXPLANATION OF NUMERALS

1: header cap
2: treated liquid outflow opening
3: treated liquid inflow opening
4: outlet opening-side filter
5: inlet opening-side filter
6: casing
7: adsorbent
8: blood purification column
9: syringe for air injection
10: pump
11: beaker
12: pure water
13: one-side mesh-equipped column
14: bath (37° C.)
15: beaker for disposal
16: blood plasma for circulation
17: blood plasma for clearance measurement

DETAILED DESCRIPTION

Our blood purification column is a column that has an adsorbent that fills the column and a filter for retaining the adsorbent, wherein the opening rate of the filter is greater than or equal to 5% and less than or equal to 80%.

Herein, as a measurement method for the opening rate of the filter, optical microscopic observation is performed to arbitrarily observe a range enclosed by a 5 mm square from the direction in which bloodstream flows through the filter when the filter is disposed in the column, that is, if there are a blood inflow opening and an outflow opening at two ends of the column, from the same direction as the direction from the inlet opening toward the outlet opening, and then the area taken up by a structural body that constitutes the filter contained in that range is assumed to be A mm² so that the representation can be made by the following expression.

$$\text{Opening rate } (\%) = (25-A)/25 \times 100$$

This is performed by selecting arbitrary five 5-mm square ranges on one filter as an object, carrying out the measurement, and then finding an average value. Incidentally, the calculated opening rate is rounded off from the first decimal place.

If the opening rate is excessively high, the strength becomes insufficient so that it becomes difficult to stably retain the adsorbent in the casing. On the other hand, if the opening rate is excessively low, the resistance against flow increases, and the air removal characteristic deteriorates. Furthermore, it becomes likely that there will be caused an increase of pressure loss at the time passage of blood in the column and a rise of the column pressure when a thrombus or the like forms in the filter. From what has been described above, the upper limit of the opening rate is less than or equal to 80%, preferably less than or equal to 70%, and more preferably less than or equal to 66%. On the other hand, the lower limit thereof is greater than or equal to 5%, preferably greater than or equal to 16%, and more preferably greater than or equal to 21%.

Furthermore, the aforementioned equivalent diameter of the aperture of the filter is an important factor. A measurement method for the equivalent diameter of the aperture is as described below. That is, when the aperture of the filter is uniform in the thickness direction, the filter is observed from the thickness direction under an optical microscopy. When the aperture of the filter is non-uniform in the thickness direction, a portion of the filter where the aperture becomes the smallest is sliced with a cutter or the like, and then subjected to observation under an optical microscopy from the aforementioned perpendicular direction in substantially the same manner, and 30 void space portions of the filter are arbitrarily extracted. The areas S of the individual portions are measured, and the equivalent diameter of the aperture of each portion is calculated by the following expression. After that, an average of the 30 measurements is calculated, and is rounded off from the first decimal place.

$$\text{The equivalent diameter of the aperture} = 2 \times (S/\pi)^{1/2}$$

It becomes difficult to retain the adsorbent within the column if the equivalent diameter of the aperture is excessively large. Furthermore, the possibility of the filter being unable to catch an extraneous matter increases if such a matter occurs in the circuit or the column increases. Therefore, specifically, the equivalent diameter of the aperture is preferred to be less than or equal to ten times the sectional area per piece of adsorbent 1 in a view of the column in the longitudinal direction, more preferably less than or equal to 5 times, and even more preferably less than or equal to 2.8 times. The sectional area per piece of adsorbent mentioned herein is, for example, in a solid yarn, the sectional area of a cross section per yarn. In spherical beads, the sectional area per piece of adsorbent is the area of a surface obtained when a bead is cut along a straight line that passes a center portion of the bead. On the other hand, if the equivalent diameter of the aperture of the filter is excessively small, the resistance against flow increases and the air removal characteristic decreases. Furthermore, it becomes likely that there will be caused an increase of pressure loss at the time passage of blood in the column and a rise of the column pressure when a thrombus or the like forms in the filter.

From what has been described above, the upper limit of the equivalent diameter of the aperture is less than or equal to 5000 μm, preferably less than or equal to 800 μm, and more preferably less than or equal to 400 μm. The lower limit of the equivalent diameter of the aperture is greater than or equal to 1 μm, preferably greater than or equal to 5 μm, and more preferably greater than or equal to 10 μm.

Figure 2:
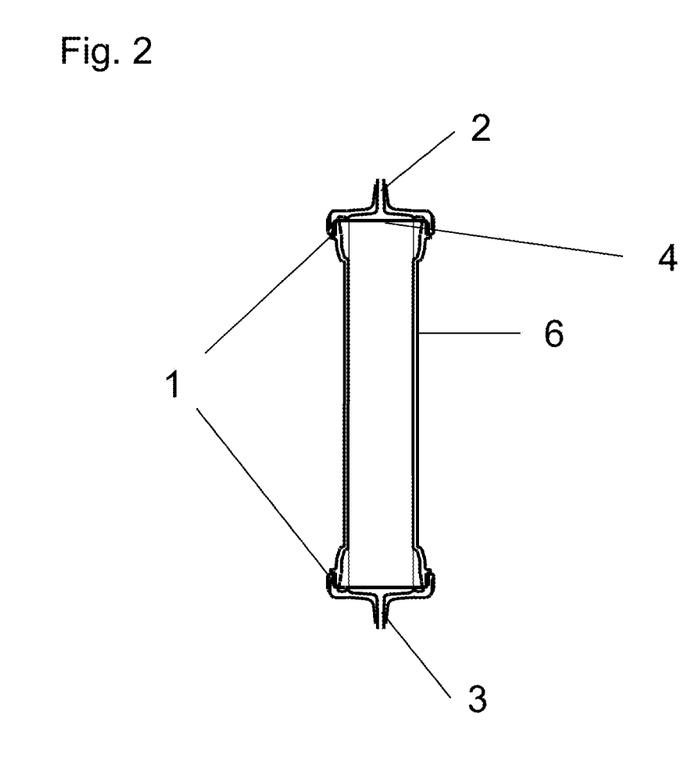
FIG. 2 is a diagram concerning a one-side mesh-equipped column.
Figure 3:
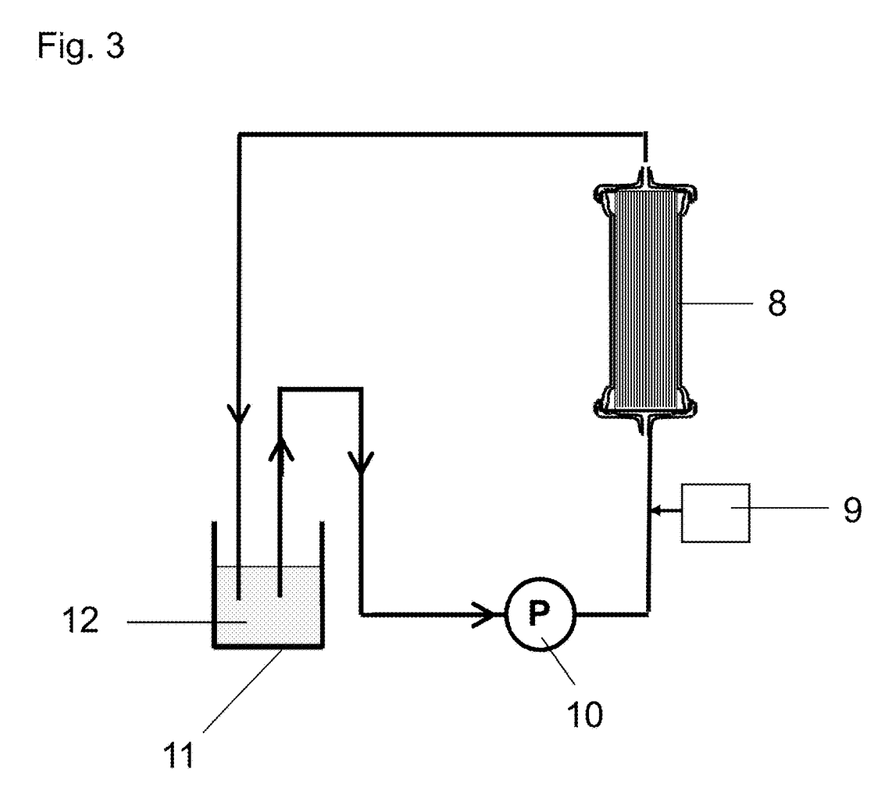
FIG. 3 is a circuit diagram concerning air removal rate measurement regarding the inside of the column in which an adsorbent is contained.
Figure 4:
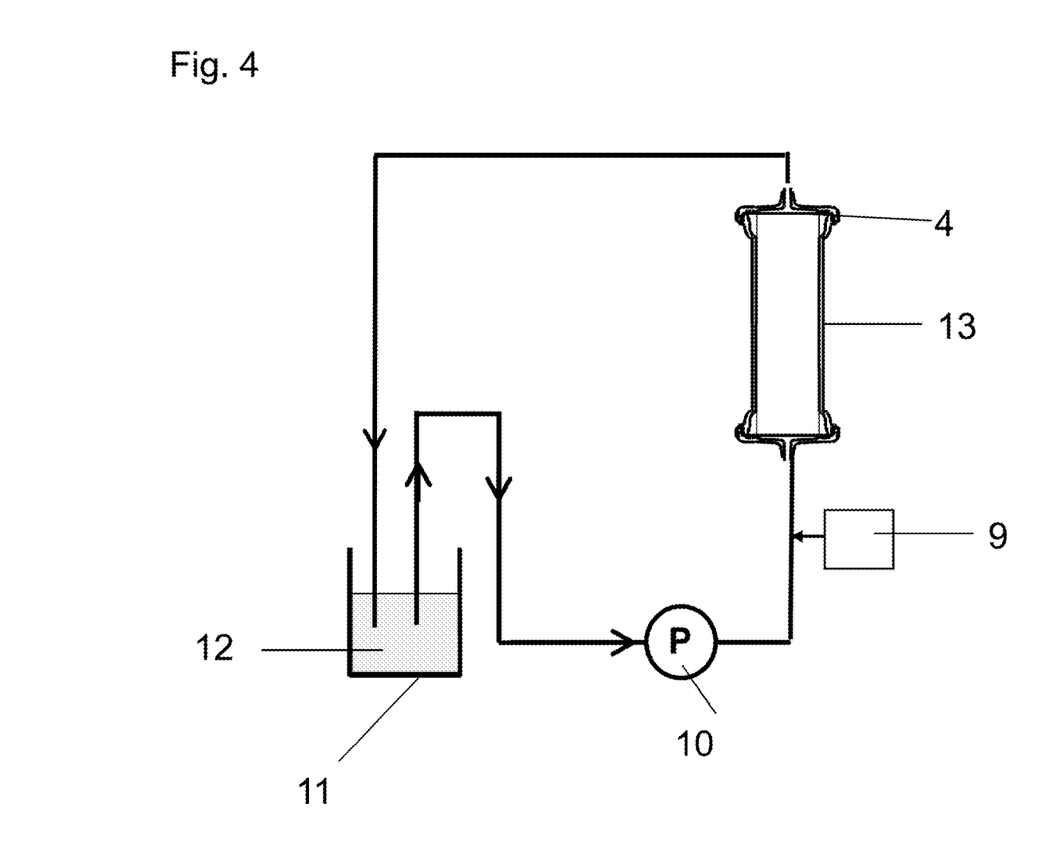
FIG. 4 is a circuit diagram concerning the air removal rate measurement regarding the inside of a one-side mesh-equipped column.

Furthermore, the air removal characteristic can be evaluated by a technique as indicated below. The two ends of the blood purification column were provided with filters and header caps that have an inflow opening and an outflow opening for a treated liquid and, subsequently, the column interior was washed with pure water, and then each port was sealed with a cap. This column is set in a circuit for testing the air removal characteristic as shown in FIG. 2 so the lengthwise direction is perpendicular to the ground surface, the rate of removal of in-column air trapped on a mesh is measured five times in the following procedure, and an average thereof is found by rounding off the first decimal place.

(1) Pure water is circulated at a flow rate of 100 ml/s by using a pump, until air in the circuit is completely removed. Air is completely driven out by, for example, tapping the column, according to need.
(2) The pump is stopped, and the column is detached from the circuit while attention is being paid so that air does not mix in, and then lids are placed on the inflow opening and the outflow opening for the treated liquid. The column weight at this time is measured and named A.
(3) The column, after the measurement of the weight, is returned to the circuit, and pure water is circulated through at a flow rate of 100 ml/s.
(4) 10 ml of dry air is injected by taking a time of 5 seconds through the use of a syringe from a site that is 1 cm toward an upstream portion from the treated liquid inflow opening of the column.
(5) Immediately, pure water is circulated at a flow rate of 100 ml/s for 1 minute. During this time, the circuit is in a state of being left standing.
(6) The pump is stopped, and the column is detached from the circuit while attention is being paid so that air does not mix in, and then lids are placed on the inflow opening and the outflow opening for the treated liquid. The column weight at this time is measured and named B.
(7) An in-column air removal rate is calculated from the expression below.

The in-column air removal rate $(\%)=(A-B)/A \times 100$

Incidentally, the air removal rate mentioned herein is preferably greater than or equal to 43%, more preferably greater than or equal to 55%, and even more preferably greater than or equal to 63%.

The adsorbent, like the adsorbent in medical appliances as mentioned above, is one that adsorbs and removes removal-object substances in blood. The form of the adsorbent to be packed may be any shape such as flat membrane states, powder states spherical particles, fractured particles, massive continuous bodies, fibrous states, tubular states, hollow yarn states, solid yarn states, granular states, platy states, fractured hollow yarn states, fractured solid yarn states and the like. In particular, if the adsorbent is in a tubular state, a hollow yarn state, or a solid yarn state of a straight shape disposed parallel in the column lengthwise direction, the flow passes also have a straight shape and, furthermore, the flow pass length can be minimized. Therefore, air is unlikely to be trapped, which is preferable. Furthermore, when the adsorbent is in a hollow yarn state or a solid yarn state, if a form of great membrane thickness portions or of portions inside the yarns is made porous, an adsorption area can be sufficiently secured, and adsorption target substances contained in blood can be efficiently adsorbed and removed and, furthermore, compared to the ultrathin fiber, fractured hollow yarn, the fractured solid yarn and the like, there is an advantage of being able to be used even when the treated liquid such as whole blood of a patient, is high in viscosity so that the risk of coagulation in the column is high. Furthermore, particularly preferable is the solid yarn state. This is because in the hollow yarn, if the pressure loss differs between the inside and the outside of the hollow yarn, there is a concern that a difference in the amount of flow of the treated liquid might occur between the outside and the inside of the hollow yarn, which, as a result, might cause a decline in the adsorption efficiency of the column. Furthermore, if the pressure losses outside and inside the hollow yarn are to be made substantially equal, great restrictions occur regarding the inside diameter of the hollow yarns and the column filling factor. Furthermore, when blood is caused to flow through the column filled with hollow yarns, the hollow portions of the hollow yarns provide a fixed and closed environment compared to the environment outside the hollow yarns in the column, which gives rise a concern that thrombus or the like might easily form. Incidentally, vacant spaces outside the hollow yarns deform as yarns move within the column and, therefore, are not a fixed and closed environment.

The straight shape mentioned herein disposed parallel with the column lengthwise direction is a shape in which the two side end surfaces of a yarn are in contact with the inlet opening and outlet opening end surfaces of the column, with a shortest possible distance. However, it is permissible that the yarns have been subjected to crinkling such as crimping. Furthermore, as for the porous adsorbent, its porous structure is preferred to uniform in the thickness direction. Due to this, the area that contributes to adsorption can be increased. On another hand, the pore structure has an asymmetrical structure with a gradient or a structure that is irregular in the thickness direction sees a decrease in the specific surface area of the adsorbent and, therefore, is not preferable.

In a yarn having been subjected to crinkling such as crimping, the yarn length is measured in a state in which the yarn is in a straight shape with the two ends stretched to find the filling factor described below. As a measurement method for the lengthwise-direction length of straight shape yarns contained in the column, a tip of a yarn taken out of the column is fixed by a tape or the like and the other tip is provided with a weight of about 3 g, and then the full length of the yarn when it is straight is promptly measured. This measurement is performed arbitrarily on 30 of the yarns in the column, and an average value for the 30 yarns is calculated.

Furthermore, the ratio of the equivalent diameter of the filter aperture to the average circle equivalent diameter of void spaces of the adsorbent is greater than or equal to 45%, preferably greater than or equal to 50%, and even more preferably greater than or equal to 56%. The aforementioned ratio is preferably less than or equal to 400%, more preferably less than or equal to 280%, and even more preferably less than or equal to 220%. The average circle equivalent diameter De mentioned herein is represented by the following expression when the adsorbent has a straight shape of arrangement in parallel with the column lengthwise direction as in the tubular state, the hollow yarn state, the solid yarn state and the like as stated in "Chemical Engineering and Artificial Organs, 2nd ed.", Kyoritsu Shuppan, 1997. pp. 162 to 163.

The average circle equivalent diameter De of adsorbent void spaces=$4 \times Af/Wp$ In the expression, Af is the flow path sectional area, which is a value obtained by subtracting, from the sectional area of a section in a direction perpendicular to the lengthwise direction of the casing, a total sum of the sectional areas of sections in the same direction which the adsorbent occupies. The total sum of the sectional areas that the adsorbent occupies can be found on the basis of the yarn diameter D0 obtained by a measurement method for the yarn diameter described below and the number of column-filling yarns N, by using the following expression.

The total sum of sectional areas occupied by the adsorbent=$(D0/2)^2 \times \pi \times N$ Furthermore, Wp is the wetted perimeter, which is the sum of the inside surface area of the casing and the total surface area of the adsorbent. The total surface area of the adsorbent can be found on the basis of the yarn diameter D0, the number of column-filling yarns N, and the lengthwise length L of yarns, by using the following expression.

The total surface area of the adsorbent=$D0 \times \pi \times L$

As for the shape of the casing, the two ends are open ends, and there can be cited, for example, a circular cylinder and a polygonal cylinder such as a quadrangular cylinder and a hexagonal cylinder. Among such, a circular cylinder and particularly a circular cylinder whose section is perfectly circular. This is because a casing having no angle can restrain residence of blood in an angle portion. Furthermore, due to both sides being open ends, the flow of blood is less likely to form an eddy diffusion, and therefore can minimize the pressure loss. Furthermore, the casing is preferred to be an instrument constructed of plastic, metal or the like. In plastic, for example, a thermoplastic resin excellent in mechanical strength and thermal stability is used. As specific examples of such a thermoplastic resin, there can be cited polycarbonate-based resin, polyvinyl alcohol-based resin, cellulose-based resin, polyester-based resin, polyalylate-based resin, polyimide-based resin, cyclic polyolefin-based resin, polysulfone-based resin, polyether sulfone-based resin, polyolefin-based resin, polystyrene resin, polyvinyl alcohol-based resin, mixtures of these. Among these, polystyrene, polycarbonate, and their derivatives are preferable in terms of the formability, the transparency and the radiation resistance required of the casing. The resin excellent in transparency allows internal states to be checked at the time of hemoperfusion, and is therefore convenient for securing safety, and the resin excellent in radiation resistance is preferable when radiative irradiation is performed at the time of sterilization. In the former, the instrument is manufactured by injection molding through the use of a die or by cutting a raw material. In the latter, the instrument is manufactured by cutting a raw material. Among such, plastic is suitably used from the viewpoint of cost, moldability, weight, and blood suitability.

Furthermore, when the adsorbent is in a form that is not the straight shape relative to the in-column blood stream direction such as the particle state, the powder state, or the fractured yarn state, the average circle equivalent diameter De can be found by the following expression.

The average circle equivalent diameter De of adsorbent void spaces=$(32 \times \mu \times L \times u/\Delta P)^{1/2}$ In the expression, $\mu$ is the viscosity of the treated liquid, L is the lengthwise-direction length of the adsorbent, u is an in-column average flow rate, and $\Delta P$ is a value obtained by subtracting the pressure loss in the column outflow portion from the pressure loss in the column inflow portion.

When the ratio of the equivalent diameter of the filter aperture to the average circle equivalent diameter of void spaces of the adsorbent is less than 45%, the aperture of the filter is conspicuously small relative to the sectional area of air that passes in the column so that there is a tendency that the passage through the filter is difficult and air easily resides in the column. On another hand, when the ratio of the equivalent diameter of the filter aperture to the average circle equivalent diameter of void spaces of the adsorbent is greater than 400%, the adsorbent easily flows out through the filter aperture, and there are cases where the adsorbent in the column is hard to retain. The calculated equivalent diameter of the aperture is rounded off from the first decimal place before the aforementioned ratio is calculated.

Furthermore, when hollow yarns or solid yarns are packed as the adsorbent, if the yarn diameter thereof (the yarn outside diameter in hollow yarns) is excessively small, there is a risk of an increase in the pressure loss in the column or of yarns themselves passing through the filter. On another hand, when the yarn diameter is excessively large, the contact area between the adsorbent and blood decreases, deteriorating the efficiency of blood purification. Therefore, the yarn diameter is preferably less than or equal to 1000 µm, more preferably less than or equal to 450 µm, even more preferably less than or equal to 280 µm, and, as the lower limit, is preferably greater than or equal to 5 µm, more preferably greater than or equal to 30 µm, and even more preferably greater than or equal to 70 µm.

As for the measurement method for the yarn diameter, of the yarns packed in the column, fifty yarns are arbitrarily extracted. After the yarns are washed, complete replacement with pure water is performed, and the yarns are sandwiched between a slide glass and a cover glass. Diameters of yarns (diameters of outermost circumferences) are measured at two locations arbitrarily on each yarn by using a projector (e.g., V-10A by Nikon Company), and an average value thereof is adopted and rounded off from the first decimal place. Incidentally, when the number of hollow yarns packed is less than 50, all the yarns are subjected to measurement, and an average value is adopted in substantially the same manner.

Furthermore, from the viewpoint of preventing the adsorbent from flowing out due to the bloodstream, the aperture of the filter is preferred to be set to such a degree as to allow blood to pass but not to allow the adsorbent to pass. That is, the aperture is preferred to be less than or equal to the diameter per piece of the adsorbent.

As the raw material of the filter, metal materials such as aluminum, natural materials such as silk, high-molecular compounds and the like can be used singly or in combination. Among such, high-molecular compounds are suitably used from the viewpoint of cost, strength, weight, biocompatibility and the like. In particular, the raw material of the filter is preferred to contain at least one kind of raw material selected from polyolefin-based resin, polyamide-based resin and fluorine-based resin. As a reason for this, a requirement of control of hydrophilicity and -phobicity regarding the filter of the blood purification column can be cited. That is, if a raw material with a high contact angle between the filter material and water is used, the removal characteristic of air having flowed into the column can be improved. As for the contact angle between the filter and water, excessively small contact angle causes a tendency that the air removal characteristic deteriorates and air remains in the column. On the other and, if the contact angle is excessively large, unspecific adsorption of protein or the like to the filter occurs, which induces attachment of thrombocytes and the like, thereby causing blood coagulation or the like. Therefore, the upper limit of the contact angle is preferably less than or equal to 125°, more preferably less than or equal to 108°, and particularly preferably less than or equal to 104°. On the other hand, the lower limit thereof is preferably greater than or equal to 66°, more preferably greater than or equal to 72°, and particularly preferably greater than or equal to 82°.

Herein, since the contact angle of a structural body such as the filter is affected by the fiber diameter and fiber density, the contact angle between the filter material and water refers to the angle inside a liquid obtained by measuring the angle between the surface of the liquid and a film surface of a uniform film after creating the film from the same raw material as the filter which film. Specifically, the film is created by creating a solution of the film dissolved in a good solvent thereof, pouring the solution into a dish made of aluminum, and evaporating the good solution for solidification in a dry atmosphere.

Measurement of the contact angle can be carried out at room temperature (23° C.) by using a contact angle meter (e.g., DropMaster DM500 by Kyowa Interface Science Company). For the calculation, a droplet method can be used in which a droplet of 2 µL is formed and caused to contact a substrate by using a syringe, and an angle formed by a liquid droplet-substrate interface and a tangent line to the liquid droplet drawn from a contact point of three phases that are the substrate surface, the droplet and a gas phase. Furthermore, as for measurement values, the contact angle is measured at 10 locations on each substrate, and an average value is found. Incidentally, the calculate contact angle is rounded off from the first decimal place.

Note herein that the improvement in the air removal characteristic by increase of the contact angle can be explained on the basis of a decrease in the interfacial tension between a solid and air. That is, when water contacts a surface of a solid, equilibrium of forces can be represented by the following expression, where the tension of the interface between the solid and the air is $\gamma 1$, the tension of the interface between water and the solid is $\gamma 2$, the tension of the interface between the water and the air is $\gamma 3$, and the angle formed by a tangential direction of the gas-liquid interface and the direction of the solid-liquid interface is $\theta$.

$$\gamma 1 = \gamma 3 \times \cos\theta + \gamma 2$$

Herein, $\theta$ is the contact angle, and $\gamma 1$ can be decreased by increasing the contact angle.

As examples of high-molecular compounds whose contact angle is greater than or equal to 66° and less than or equal to 125°, there can be cited (metha)acryl-based resin, olefin-based resin, silicone-based resin, polyvinyl chloride-based resin, polychlorinated vinylidene-based resin, fluorine-based resin, polyester-based resin, mixtures of these and the like. Among such, the polyolefin-based resin, the polyamide-based resin, and the fluorine-based resin can be suitably used from the viewpoint of the cost and the ease of forming at the time of production, and the durability to the sterilization process. More preferable are polypropylene, polyethylene, nylon 6, nylon 66, and derivatives of these. Particularly preferable are polypropylene and its derivatives.

Furthermore, the form of the filter may be either a madreporic body or a porous body. However, a porous body in which pores are uniformly provided is preferably used, and there can be cited a mesh, a non-woven fabric and the like. Among such, the mesh is suitably used from the standpoints that since the aperture is uniform, attachment of blood corpuscle components is less, and that occurrence of elutes from the filter is unlikely.

Furthermore, in the filter, for the purpose of preventing local deterioration of the air removal characteristic, it is preferable that uniform opening portions are provided in the entire film. Herein, that uniform opening portions are provided in the entire filter refers to a filter in which, when the opening rate is not constant, no matter which arbitrary 5-mm-square ranges are selected in the entire film, the width of variation of the value of the opening rate is contained in the range of less than or equal to ±30% of the average value, more preferably less than or equal to ±18%, and even more preferably less than or equal to ±10%.

As for the thickness of the filter, excessive thickness leads to a decrease in the filling factor of the adsorbent in the column so that the blood purification efficiency will decrease. Furthermore, the pressure loss at the time passage of blood in the column also increases. On the other hand, if the filter is excessively thin, the strength of the filter becomes insufficient so that it becomes difficult to stably retain the adsorbent in the casing. From what is described above, the upper limit of the thickness of the filter is preferred to be less than or equal to 3000 µm, and more preferably less than or equal to 900 µm. The lower limit of the thickness of the filter is preferred to be greater than or equal to 0.1 µm, and more preferably greater than or equal to 40 µm.

Furthermore, as for the filter retained in the column, it is preferable that when the surface area of a portion open in a perpendicular direction relative to the longer-axis direction in the column is B1 and the total surface area of a portion open in a direction other than the perpendicular direction relative to the in-column longer-axis direction is B2, the area of B2 be made as small as possible. It is conceivable to use a filter open in a direction other than the perpendicular direction relative to the longer-axis direction in the column for the purpose of stably retaining the adsorbent in the column by using the filter or the purpose of improving the in-column flow by using the filter as a spacer. However, such a mesh easily inhibits the flow of air that flows in adsorbent void spaces, and easily traps air so that it is not preferable. Furthermore, due to this, there is a possibility that the amount of adsorbent that can be packed in the column will decrease, leading to a decrease in adsorption performance. Specifically, it is preferable to satisfy a relation of B1/B2≥1.0, more preferably B1/B2≥5.0, and even more preferably B1/B2≥10.0. When a portion is open in an oblique direction that is not perpendicular nor parallel to the in-column longer-axis direction, the portion is not included in either the denominator nor the numerator.

As the form of a column equipped with the filter, the column is usually made up of a casing provided with an inlet opening portion through which pre-purification bloodstream flows in and an outlet opening portion through which post-purification bloodstream is let out, an adsorbent housed in the casing, a filter provided inside an inlet opening portion and/or an outlet opening portion, and header caps disposed at two ends in a casing lengthwise direction and provided with an inflow opening and an outflow opening for blood. In connection with retaining the adsorbent within the casing, it is preferable to provide a filter in each of the inlet opening and the outlet opening on the two sides. However, when the adsorbent can be retained at only one of the inlet opening and the outlet opening, a filter may be used on only one side, that is, it is permissible to dispose a filter at one side of the column and a filter different from the filter at the opposite side.

The upper limit of the filling factor of the adsorbent in the casing of the column is preferred to be less than 70% and more preferably less than or equal to 63%. The lower limit of the filling factor of the adsorbent is preferred to be greater than or equal to 13%, more preferably greater than or equal to 30%, and particularly preferably greater than or equal to 45%. Because the filling factor of the adsorbent is greater than or equal to 13%, the blood volume needed for blood purification is reduced so that the burden on patients can be alleviated. On the other hand, if the filling factor of the adsorbent is greater than or equal to 70%, the air removal characteristic deteriorates. Furthermore, the packing of the adsorbent becomes harder so that a decrease in operation efficiency is brought about. Incidentally, the filling factor mentioned herein refers to the proportion accounted for by the adsorbent volume to the casing volume provided with the inlet opening portion through which the pre-purification bloodstream flows in and the outlet opening portion through which the post-purification bloodstream is let out, and does not factor in the aforementioned header portion.

Hereinafter, in conjunction with creation examples of the blood purification column, an example that has used an adsorbent of the solid yarn as a yarn state is shown. However, this does not limit this disclosure.

A spinning stock liquid in which a polymer is dissolved in a solvent is prepared. The spinning stock liquid is discharged from a spinneret nozzle that has a circular stock liquid discharge opening, and is coagulated into a solid yarn shape in a solidification bath. The solidification bath is usually made up of a coagulation agent such as water or alcohol, or a mixture with a solvent that constitutes the spinning stock liquid. Furthermore, the porosity can be changed by controlling the temperature of the solidification bath. Since the porosity can be affected by the kind of spinning stock liquid or the like, the porosity can be increased typically by increasing the temperature of the solidification bath, which is selected as appropriate. Although the mechanism for this is not precisely clear, it can be considered that, in the desolvation from the stock liquid and the competing reactions of desolvation from the stock liquid and solidification shrinkage, the desolvation may be faster in a high-temperature bath and therefore the solidification fixation occurs before shrinkage. However, if the solidification bath temperature becomes excessively high, the pore diameter becomes excessively large. Therefore, for example, the solidification bath temperature when the solid yarn is a yarn containing polymethyl methacrylate (hereinafter, PMMA) and gas is put in the inner tube is preferred to be greater than or equal to 39° C., and more preferred to be greater than or equal to 42° C. On the other hand, the solidification bath temperature is preferred to be less than or equal to 50° C. and more preferably less than or equal to 46° C.

Next, a process of washing off the solvent attached to the solidified solid yarn is passed through. The means of washing the solid yarn is not particularly limited. However, a method in which the solid yarn is passed through a bath having multiple stages that hold water (referred to as rinsing bath) is preferred. It suffices that the temperature of water in the rinsing bath is determined according to the property of the polymer that constitutes the yarn. For example, in a yarn containing PMMA, a water temperature of 30 to 50° C. is used.

Furthermore, as for the solid yarn, to retain the pore diameter after the rinsing bath, a process of imparting a moisturizing component may be included. The moisturizing component mentioned herein refers to a component capable of maintaining the degree of moisture of the solid yarn or a component capable of preventing decrease of the degree of moisture of the solid yarn. As representative examples of the moisturizing component, there are glycerin and its aqueous solution.

To increase the dimensional stability of the solid yarn, which is high in shrink characteristic, after the rinsing and the moisturizing component impartation have ended, a process of a bath filled with a heated aqueous solution of a moisturizing component (referred to as a heat treatment bath) can be passed through. The heat treatment bath is filled with a heated aqueous solution of the moisturizing component. The solid yarn, due to passing through this heat treatment bath, receives thermal operation and shrinks so that the solid yarn comes to less easily shrink in the following processes and thus the yarn structure can be stabilized. This heat treatment temperature varies depending on the yarn raw material. However, in a yarn that contains PMMA, the heat treatment temperature is preferred to be greater than or equal to 75° C., and more preferred to be greater than or equal to 82° C. Furthermore the heat treatment temperature is preferred to be less than or equal to 90° C., and temperatures less than or equal to 86° C. are set as more preferable temperatures.

An example of how to form a purification column by using the solid yarn obtained will be indicated as follows.

Figure 1:
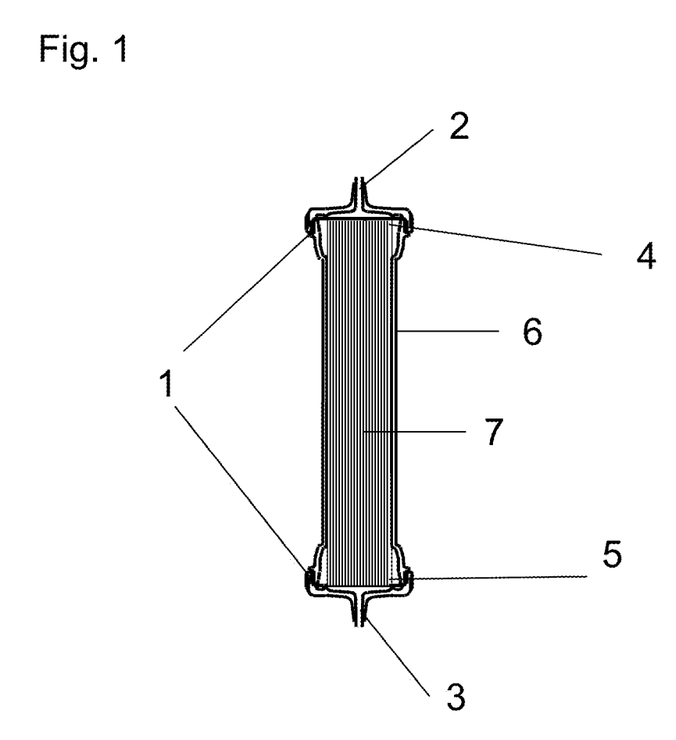
FIG. 1 is a diagram concerning a column that contains an adsorbent.

First, the solid yarn is cut to a needed length. After a needed number of yarns are bundled, the bundle of yarns is put into the plastic casing, which forms a cylinder portion of the blood purification column. After that, the two ends of the solid yarns are cut by a cutter or the like so that the solid yarns can be housed within the casing, and the outflow and inflow openings for the treated liquid provided at the column's two side end surfaces at the column's two ends are provided with mesh filters that have been cut to a diameter equal to the inside diameter of the ends as indicated in FIG. 1. Finally, inlet opening and outlet opening ports for the treated liquid which are called header cap are attached so that a blood purification column can be obtained.

Furthermore, in use as medical devices or the like, using it after disinfecting or sterilizing is preferable. As disinfection or sterilization methods, various disinfection and sterilization methods, for example, high pressure steam sterilization, gamma ray sterilization, ethylene oxide gas sterilization, agent disinfection, ultraviolet ray disinfection and the like, can be exemplified. Of these methods, the gamma ray sterilization, the high-pressure steam sterilization, and the ethylene oxide gas sterilization have less effect on the sterilization efficiency and the materials, and are preferable.

As the form in which the blood purification column is used, a technique in which the blood purification column is incorporated in an extracorporeal circulation circuit and adsorption removal is performed on-line is preferable from the viewpoint of the amount of processing in one run, the ease of operation and the like. In this case, the purification column may be used singly or may also be connected in series to an artificial kidney or the like at the time of dialysis or the like and used simultaneously therewith.

EXAMPLES

Example 1

31.7 parts by weight of syn-PMMA having a weight-average molecular weight of 400 thousand, 31.7 parts by weight of syn-PMMA having a weight-average molecular weight of 1.4 million, 16.7 parts by weight of iso-PMMA having a weight-average molecular weight of 500 thousand, and 20 parts by weight of PMMA copolymer having a molecular weight of 300 thousand and containing 1.5 mol % of sodium para-styrene sulfonate were mixed with 376 parts by weight of dimethyl sulfoxide, and stirring was performed at 110° C. for 8 hours to prepare a spinning stock liquid. The viscosity of the obtained spinning stock liquid at 110° C. was 1240 poise. The obtained spinning stock liquid was discharged into air at a rate of 1.0 g/min from a spinneret nozzle having a circular discharge opening of 0.3 mm in diameter which was kept at a temperature of 93° C., and was guided into a solidification bath after a run of 50 cm in air. The temperature of water used for the solidification bath (solidification bath temperature) was set at 42° C., and solid yarns were obtained. After the individual solid yarns were rinsed, glycerin in the form of a 70 wt % aqueous solution was imparted as a moisturizing agent. Then, the heat treatment bath temperature was set at 84° C., and the extraneous glycerin was removed. Then, a spacer yarn was wound around to perform wind-up at 42 m/min. The yarn diameter of the solid yarn obtained was measured by using a projector V-10A by Nikon Company. A result was 121 μm.

The obtained solid yarns were bundled by using a publicly known method, and solid yarns having a yarn diameter of 121 μm were contained in a cylindrical casing made of polycarbonate having an inside diameter of 38 mm and an axis-direction length of 133 mm so that the filling factor was 57%. Next, mesh filters made of polypropylene having an aperture equivalent diameter of 84 μm and an opening rate of 36% which had been cut to a diameter comparable to the casing's inside diameter as shown in FIG. 1 were attached to the outflow and inflow openings for a treated liquid at two side end surfaces of the column. The equivalent diameter and the opening rate of the aperture of the filter and the filling factor of the column were calculated by the techniques described above after measurement was performed by using a projector V-10A by Nikon Company.

Furthermore, header caps having an inflow opening or an outflow opening for the treated liquid were disposed on the column's two ends. Subsequently, the column's interior was washed with pure water, and then each port was sealed with a cap. Thus, a column equipped with meshes at the two sides was created. The average circle equivalent diameter of adsorbent void spaces of this column was 91 μm. This column was set in a circuit for testing the air removal characteristic as in FIG. 2 so that the lengthwise direction of the column was perpendicular to the ground. A removal rate for in-column air trapped by the mesh was measured by the following procedure.

(1) Pure water was circulated at a flow rate of 100 ml/s by using a pump until air in the circuit was completely removed. Driving out air was facilitated by giving the column an impact such as tapping the column according to need.
(2) The pump was stopped, and the column was detached from the circuit while attention was being paid so that air did not mix in, and then lids were placed on the inflow opening and the outflow opening for the treated liquid. The column weight at this time was measured and named A.
(3) The column, after the measurement of the weight, was returned to the circuit, and pure water was circulated through at a flow rate of 100 ml/s.
(4) 10 ml of dry air was injected by taking a time of 5 seconds through the use of a syringe from a site that was 1 cm toward an upstream portion from the treated liquid inflow opening of the column.
(5) Immediately, pure water was circulated at a flow rate of 100 ml/s for 1 minute. During this time, the circuit was in a state of being left standing.
(6) The pump was stopped, and the column was detached from the circuit while attention was being paid so that air did not mix in, and then lids were placed on the inflow opening and the outflow opening for the treated liquid. The column weight at this time was measured and named B.
(7) An in-column air removal rate was calculated from the expression below. Results are shown in Table 1.

The in-column air removal rate $(\%) = (A-B)/A \times 100$

Example 2

Solid yarns were obtained by the same method as in Example 1, except that the discharge speed of the spinning stock liquid was set at 1.9 g/min so that the yarn diameter was 181 μm. The solid yarns were contained within a casing having the same dimensions and shape as in Example 1, in substantially the same manner as in Example 1, and mesh filters and header caps having the same dimensions and shapes as in Example 1 were disposed at the casing's two side end surfaces. The average circle equivalent diameter of adsorbent void spaces of this column was 135 μm. This column was subjected to the measurement of the in-column air removal rate in substantially the same procedure as in Example 1. Results are shown in Table 1.

Example 3

Solid yarns were obtained by the same method as in Example 1, except that the discharge speed of the spinning stock liquid was set at 0.5 g/min so that the yarn diameter was 56 μm. The solid yarns were contained within a casing having the same dimensions and shape as in Example 1, in substantially the same manner as in Example 1, and mesh filters and header caps having the same dimensions and shapes as in Example 1 were disposed at the casing's two side end surfaces. The circle average equivalent diameter of adsorbent void spaces of this column was 42 μm. This column was subjected to the measurement of the in-column air removal rate in substantially the same procedure as in Example 1. Results are shown in Table 1.

Example 4

Solid yarns were obtained by the same method as in Example 1, and were contained within a casing having the same dimensions and shape as in Example 1, in substantially the same manner as in Example 1. Mesh filters made of polypropylene and having an aperture equivalent diameter of 124 μm and an opening rate of 31% and header caps having the same dimensions and shape as in Example 1 were disposed at the casing's two side end surfaces in substantially the same manner as in Example 1. The circle average equivalent diameter of adsorbent void spaces of this column was 91 μm. This column was subjected to the measurement of the in-column air removal rate in substantially the same procedure as in Example 1. Results are shown in Table 1. Furthermore, to evaluate the protein removal performance of the obtained purification column, a clearance measurement for $\beta^2$-MG (microglobulin) was performed by a method indicated below. Results are shown in Table 3.

Measurement Method for Clearance of $\beta^2$-MG

For performance evaluation of the adsorption column, clearance of $\beta^2$-MG was performed. $\beta^2$-MG is known to be a protein that causes dialysis-related amyloidosis, which is a long-term dialysis complication.

A bovine blood to which ethylenediaminetetraacetic acid disodium had been added was prepared so that the hematocrit was 30±3% and the total protein amount was 6.5±0.5 g/dL. Bovine blood within 5 days following collection of the blood was used.

Next, $\beta^2$-MG was added and stirring was performed so that the $\beta^2$-MG concentration was 1 mg/l. As for that bovine blood, 2 L was separated for circulation and 1.5 L for clearance measurement.

Figure 5:
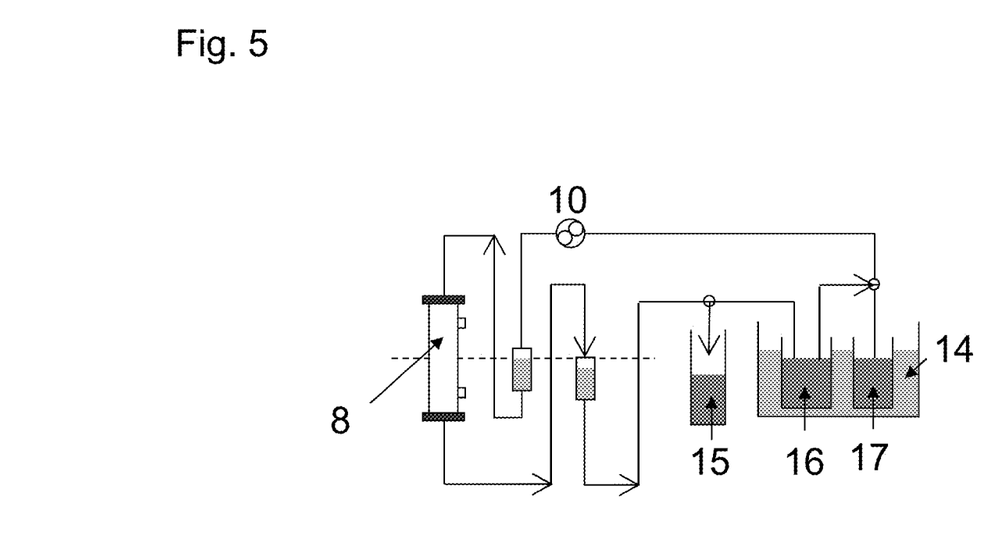
FIG. 5 is a circuit diagram regarding β2-MG clearance measurement regarding a blood purification column.

The circuit was set as in FIG. 5. In the circuit, an inlet opening portion that takes up the treated liquid was named Bi, and an outlet opening portion the liquid having passed through the blood purification column was named Bo.

The Bi was put into a beaker for circulation holding 2 L of bovine blood (37° C.) prepared as described above, and the pump was started with the flow rate set at 200 mL/min. After an amount of liquid over discharged from Bo for 90 seconds was discarded, the Bo was immediately put into the beaker for circulation, and a circulating state was assumed.

After circulation was performed for 1 hour, the pump was stopped.

Next, the Bi was put into the bovine blood for clearance measurement which had been prepared as described above, and the Bo was put into a beaker for disposal.

The flow rate was set at 200 mL/min. After two minutes elapsed following the starting of the pump, a sample of 10 ml was collected from the bovine blood (37° C.) for clearance measurement, and was named Bi liquid. After 4 minutes 30 seconds elapsed following the start, a sample of 10 ml that flowed out from the Bo was collected, and named Bo liquid. These samples were stored in a refrigerator at less than or equal to −20° C.

From the concentrations of $\beta^2$-MG in the liquids, the clearance was calculated by using the following I expression. Since measured values could sometimes vary depending on lots of bovine blood, the same lot of bovine blood was used for all of the examples and comparative examples.

$$Co(\text{ml/min}) = (CBi - CBo) \times Q_B / CBi \quad (I)$$

In the I expression, $Co = \beta^2$-MG clearance (ml/min), $CBi = \beta^2$-MG concentration in Bi liquid, $CBo = \beta^2$-MG concentration in Bo liquid, and $Q_B$=Bi pump flow amount (ml/min).

Example 5

Solid yarns were obtained by the same method as in Example 1, and were contained within a casing having the same dimensions and shape as in Example 1, in substantially the same manner as in Example 1. Mesh filters made of polyethylene terephthalate and having an aperture equivalent diameter of 108 μm and an opening rate of 40% and header caps having the same dimensions and shape as in Example 1 were disposed at the casing's two side end surfaces in substantially the same manner as in Example 1. The circle average equivalent diameter of adsorbent void spaces of this column was 91 μm. This column was subjected to the measurement of the in-column air removal rate in substantially the same procedure as in Example 1. Results are shown in Table 1. Furthermore, the clearance of $\beta^2$-MG was measured in substantially the same procedure as in Example 4. Results are shown in Table 3.

Example 6

Solid yarns were obtained by the same method as in Example 1, except that the discharge speed of the spinning stock liquid was set at 4.7 g/min so that the yarn diameter was 260 μm. The solid yarns were contained within a casing having the same dimensions and shape as in Example 1, in substantially the same manner as in Example 1. In substantially the same manner as in Example 5, mesh filters made of polypropylene and having an aperture equivalent diameter of 108 μm and an opening rate of 40% and header caps having the same dimensions and shape as in Example 1 were disposed at the casing's two side end surfaces in substantially the same manner as in Example 1. The circle average equivalent diameter of adsorbent void spaces of this column was 194 μm. This column was subjected to the measurement of the in-column air removal rate in substantially the same procedure as in Example 1. Results are shown in Table 1. Furthermore, the clearance of $\beta^2$-MG was measured in substantially the same procedure as in Example 4. Results are shown in Table 3.

Comparative Example 1

Solid yarns were obtained by the same method as in Example 1, except that the discharge speed of the spinning stock liquid was set at 4.7 g/min so that the yarn diameter was 260 μm. The solid yarns were contained within a casing having the same dimensions and shape as in Example 1, in substantially the same manner as in Example 1. The solid yarns were contained within a casing having the same dimensions and shape as in Example 1, in substantially the same manner as in Example 1, and mesh filters and header caps having the same dimensions and shapes as in Example 1 were disposed at the casing's two side end surfaces. The circle average equivalent diameter of adsorbent void spaces of this column was 194 μm. This column was subjected to the measurement of the in-column air removal rate in substantially the same procedure as in Example 1. Results are shown in Table 1. Furthermore, the clearance of $\beta^2$-MG was measured in substantially the same procedure as in Example 4. Results are shown in Table 3.

Example 7

A spinning stock liquid substantially the same as in Example 1 was discharged into air at a rate of 2.5 g/min from a spinneret nozzle having double-tube for hollow yarn with an annular slit portion's outside diameter/inside diameter=2.1/1.95 mmϕ which was kept at a temperature of 93° C. Here, at the same time, a nitrogen gas was injected into an inner tube portion of the double tube, and guided into a solidification bath after a run of 50 cm in air. The temperature of water used for the solidification bath (solidification bath temperature) was set at 42° C., and hollow yarn membranes were obtained. After the individual hollow yarn membranes were rinsed, glycerin in the form of a 70 wt % aqueous solution was imparted as a moisturizing agent. Then, the heat treatment bath temperature was set at 84° C., and the extraneous glycerin was removed. Then, a spacer yarn was wound around to perform wind-up at 60 m/min. The yarn diameter of the hollow yarn obtained was measured by using a projector V-10A by Nikon Company. As a result, the inside diameter was 200 μm, and the yarn outside diameter was 260 μm. The yarns were contained in a casing having the same dimensions and shape as in Example 1, in substantially the same manner as in Example 1. In substantially the same manner as in Example 6, mesh filters made of polypropylene and having an aperture equivalent diameter of 108 μm and an opening rate of 40% and header caps having the same dimensions and shape as in Example 1 were disposed at the casing's two side end surfaces in substantially the same manner as in Example 1. The circle average equivalent diameter of adsorbent void spaces of this column was 195 μm. This column was subjected to the measurement of the in-column air removal rate in substantially the same procedure as in Example 1. Results are shown in Table 1.

Reference Example 1

To the treated liquid outflow-side end surface of a cylindrical casing having an inside diameter of 46 mm and an axis-direction length of 100 mm, a mesh filter made of polypropylene and having an aperture equivalent diameter of 326 μm and an opening rate of 51% which had been cut into a cylindrical shape with its diameter being equal to the inside diameter of the outflow opening for the treated liquid was attached, as shown in FIG. 2. Furthermore, header caps having an inflow opening and an outflow opening for the treated liquid are disposed at the two ends. Thus, a one-side mesh-equipped column was created. Adsorbent was not contained. This one-side mesh-equipped column was subjected to measurement of the in-column air removal rate in substantially the same procedure as in Example 1. Results are shown in Table 2.

Reference Example 2

A one-side mesh-equipped column was created in substantially the same manner as in Reference example 1, except that, to the treated liquid outflow-side end surface of a casing having the same dimensions and shape as in Reference example 1, a mesh filter made of polytetrafluoroethylene and having an aperture equivalent diameter of 274 μm, an opening rate of 45% and a thickness of 245 mm which had been cut into a cylindrical shape with its diameter being equal to the inside diameter of the outflow opening for the treated liquid was attached. This one-side mesh-equipped column was subjected to measurement of the in-column air removal rate in substantially the same procedure as in Example 1. Results are shown in Table 2.

Reference Example 3

A one-side mesh-equipped column was created in substantially the same manner as in Reference example 1, except that, to the treated liquid outflow-side end surface of a casing having the same dimensions and shape as in Reference example 1, a mesh filter made of nylon 66 and having an aperture equivalent diameter of 274 μm, an opening rate of 37% and a thickness of 291 mm which had been cut into a cylindrical shape with its diameter being equal to the inside diameter of the outflow opening for the treated liquid was attached. This one-side mesh-equipped column was subjected to measurement of the in-column air removal rate in substantially the same procedure as in Example 1. Results are shown in Table 2.

Reference Example 4

A one-side mesh-equipped column was created in substantially the same manner as in Reference example 1, except that, to the treated liquid outflow-side end surface of a casing having the same dimensions and shape as in Reference example 1, a mesh filter made of polyethylene terephthalate and having an aperture equivalent diameter of 308 μm, an opening rate of 42% and a thickness of 280 mm which had been cut into a cylindrical shape with its diameter being equal to the inside diameter of the outflow opening for the treated liquid was attached. This one-side mesh-equipped column was subjected to measurement of the in-column air removal rate in substantially the same procedure as in Example 1. Results are shown in Table 2.

TABLE 1

| | Cylindrical casing | | | Adsorbent | | | Mesh | | | Proportion of equivalent diameter of aperture to average circle equivalent diameter of in-column adsorbent void spaces % | In-column air removal rate % |
|---|---|---|---|---|---|---|---|---|---|---|---|
| | Internal diameter mm | Length in axial direction mm | Configuration | Yarn diameter μm | Filling factor % | Circle average equivalent diameter of adsorbent void spaces (De) μm | Opening rate % | Aperture equivalent diameter μm | Material - | | |
| Example 1 | 38 | 133 | Solid yarn | 121 | 57 | 91 | 36 | 84 | Polypropylene | 92 | 89 |
| Example 2 | 38 | 133 | Solid yarn | 181 | 57 | 135 | 36 | 84 | Polypropylene | 62 | 83 |
| Example 3 | 38 | 133 | Solid yarn | 56 | 57 | 42 | 36 | 84 | Polypropylene | 198 | 100 |
| Example 4 | 38 | 133 | Solid yarn | 121 | 57 | 91 | 31 | 124 | Polypropylene | 137 | 100 |
| Example 5 | 38 | 133 | Solid yarn | 121 | 57 | 91 | 40 | 108 | Polyethylene terephthalate | 119 | 72 |
| Example 6 | 38 | 133 | Solid yarn | 260 | 57 | 194 | 40 | 108 | Polypropylene | 56 | 76 |
| Example 7 | 38 | 133 | Hollow yarn | 260 (internal diameter: 200) | 57 | 195 | 40 | 108 | Polypropylene | 55 | 79 |
| Comparative example 1 | 38 | 133 | Solid yarn | 260 | 57 | 194 | 36 | 84 | Polypropylene | 43 | 59 |

TABLE 2

| | Cylindrical casing | | Mesh | | | | In-column |
| --- | --- | --- | --- | --- | --- | --- | --- |
| | Internal diameter mm | Length in axial direction mm | Opening rate % | Aperture equivalent diameter μm | Material - | Contact angle ° | air removal rate % |
| Reference example 1 | 46 | 100 | 43 | 326 | Polypropylene | 90 | 100 |
| Reference example 2 | 46 | 100 | 45 | 274 | Polytetrafluoroethylene | 108 | 100 |
| Reference example 3 | 46 | 100 | 37 | 291 | Nylon 66 | 74 | 91 |
| Reference example 4 | 46 | 100 | 42 | 308 | Polyethylene terephthalate | 65 | 67 |

TABLE 3

| | Protein adsorption/removal performance $\beta^2$-microglobulin clearance ml/min |
| --- | --- |
| Example 4 | 52 |
| Example 5 | 50 |
| Example 6 | 27 |
| Comparative example 1 | 24 |

Based on results in Table 1, it can be understood that if the proportion of the equivalent diameter of the aperture to the average circle equivalent diameter of in-column adsorbent void spaces is greater than or equal to 45%, the in-column air removal rate attains a high value, but if the proportion is less than 45%, the in-column air removal rate exhibits a value as low as 59%. This is believed to be because when the equivalent diameter of the filter aperture is small compared to the average circle equivalent diameter of in-column adsorbent void spaces, the aperture of the filter is conspicuously small relative to the sectional area of air that passes in the column and, therefore, air is easily trapped by the filter. It is indicated that, compared to a mesh made of polyethylene terephthalate, a mesh made of polypropylene achieves a somewhat higher air removal rate.

Based on results in Table 2, it can be understood that when meshes substantially alike or identical in the opening rate and the aperture equivalent diameter, the in-column air removal rate exhibits a higher value as the contact angle is higher. This is believed to be because an increase in the contact angle decreases the tension of the interface between the solid state and air.

Based on results in Table 3, with regard to the columns alike or identical in the yarn diameter of the adsorbent and the filling factor, the relation between the in-column air removal rate and the clearance of $\beta^2$-MG was that as the in-column air removal rate was lower, the clearance of $\beta^2$-MG tended to decrease, that is, the adsorption performance for protein tended to decrease. Incidentally, in conjunction with results in Table 3, the yarn diameters of the adsorbents of the columns in accordance with Example 4 and Example 5 are 121 μm. On the other hand, the yarn diameters of the adsorbents of the columns in accordance with Example 6 and Comparative example 1 is 260 μm. Since in any one of the columns, the filling factor of the adsorbent is 57%, the columns with the yarn diameter being 121 μm and the columns with the yarn diameter being 260 μm produced differences in the protein adsorption performance due to variations in the surface area of the adsorbent per column.

The invention claimed is:

1. A blood purification column comprising an adsorbent and a casing whose two ends are open ends, wherein the adsorbent is housed inside the casing, and wherein one of two casing ends is a blood inflow-side end portion and the other of the two casing ends is a blood outflow-side end portion, and wherein a mesh filter is disposed at the blood inflow-side end portion and/or the blood outflow-side end portion of the casing, and wherein the mesh filter satisfies (1)-(6):
   (1) an opening rate thereof is greater than or equal to 21% and less than or equal to 66%;
   (2) an equivalent diameter of an aperture thereof is greater than or equal to 10 μm and less than or equal to 400 μm;
   (3) a ratio of the equivalent diameter of the aperture thereof to an average circle equivalent diameter of void spaces of the adsorbent is greater than or equal to 56% and less than or equal to 220%;
   (4) the absorbent is in a hollow yarn and/or a solid yarn form;
   (5) the adsorbent is disposed parallel to a column lengthwise direction; and
   (6) a surface area of a portion open in a perpendicular direction relative to a lengthwise direction in the column is B1 and a total surface area of a portion open in a parallel direction relative to the lengthwise direction in the column is B2, wherein B1/B2 ≥1.

2. The blood purification column according to claim 1, wherein the mesh filter contains at least one kind of raw material selected from the group consisting of a polyolefin-based resin, a polyamide-based resin and a fluorine-based resin.

3. The blood purification column according to claim 1, wherein a filling factor of the adsorbent in a housing space in the column is greater than or equal to 30% and less than 70%.

4. The blood purification column according to claim 1, wherein a yarn diameter or an outside diameter of the hollow yarn or solid yarn is greater than or equal to 10 μm and less than or equal to 1000 μm.

5. The blood purification column according to claim 1, connected in series to an artificial kidney.

6. The blood purification column according to claim 2, wherein a form of the adsorbent is a hollow yarn state and/or a solid yarn state.

7. The blood purification column according to claim 6, wherein the adsorbent in the hollow yarn state and/or the solid yarn state is disposed parallel with a column lengthwise direction.

8. The blood purification column according to claim 1, wherein the form of the adsorbent is a solid yarn state.

* * * * *